(12) United States Patent
Hossain et al.

(10) Patent No.: US 6,406,485 B1
(45) Date of Patent: Jun. 18, 2002

(54) SURGICAL GRASPING DEVICE AND COMPONENTS THEREOF

(75) Inventors: Mosaddeq Hossain, Somerville; Robert Banik, Long Valley, both of NJ (US)

(73) Assignee: Pilling Weck Incorporated, Horsham, PA (US)

( * ) Notice: Subject to any disclaimer, the term of this patent is extended or adjusted under 35 U.S.C. 154(b) by 42 days.

(21) Appl. No.: 09/680,641

(22) Filed: Oct. 6, 2000

Related U.S. Application Data

(60) Provisional application No. 60/158,324, filed on Oct. 8, 1999.

(51) Int. Cl.[7] .............................................. A61B 17/00
(52) U.S. Cl. ...................................... 606/207; 606/151
(58) Field of Search .................................. 606/207, 206, 606/205, 209, 210, 151, 157, 138, 139, 140

(56) References Cited

U.S. PATENT DOCUMENTS 5,728,121 A   3/1998   Bimbo et al.

6,206,896 B1 * 3/2001 Howell et al. ............... 606/207
6,325,810 B1 * 12/2001 Hamilton et al. ........... 606/151

* cited by examiner

Primary Examiner—Kevin T. Truong
(74) Attorney, Agent, or Firm—Howson & Howson

(57) ABSTRACT

A grasping pad assembly comprises a silicone element with a hydrophobic membrane. The silicone element is adhered to a stainless steel element having a C-shaped clip at its distal end for grasping the tip of a forceps jaw. A molded polypropylene element extends through a hole in the metal element and includes a projection which extends through an opening in the metal element near the proximal end of the pad. This projection fits into a hole in the face of the jaw of the forceps to hold the grasping pad securely to the jaw until it is forcibly removed by bending and sliding. The use of the stainless steel clip in combination with the polypropylene projection enables the thickness of the pad assembly to be minimized while obviating adherence to very close manufacturing tolerances for ensuring proper fit of the projection into the hole in the jaw.

18 Claims, 4 Drawing Sheets

SURGICAL GRASPING DEVICE AND COMPONENTS THEREOF

CROSS-REFERENCE TO RELATED APPLICATION

This application claims the benefit of provisional application No. 60/158,324, filed Oct. 8, 1999.

SUMMARY OF THE INVENTION

This invention relates to surgery and more particularly to improvements in surgical grasping devices, for example forceps and clamps.

It has long been an objective of designers of surgical forceps, clamps and similar instruments to produce an instrument that can grasp slippery tissue securely and yet not cause trauma by puncturing, shearing, stretching or exerting excessive pressure on the tissue. To this end, numerous instruments have been designed having atraumatic toothed jaws made of metal. For an early example, see U.S. Pat. No. 2,668,538, granted on Feb. 9, 1954.

More recently, there has been a trend toward the use of non-metal gripping materials such, as polyvinyldiene fluoride, which are relatively smooth and pliable, but which exhibit sufficiently high friction that they are able to grasp wet, slippery tissue effectively. Such materials are particularly suited to use in disposable attachments to the jaws of grasping instruments, as described in U.S. Pat. No. 5,728,121, dated Mar. 17, 1998.

A trend toward minimally invasive surgery using laparoscopic instruments has given rise to efforts on the part of instrument designers to produce very small instrument jaws and disposable jaw attachments. The jaws and jaw attachments are desirably made as small as possible in size, so that they can pass through small incisions, or through very narrow passages in cannulae used in gaining access to various internal organs, vessels and other tissues.

Heretofore, practical jaw attachments have generally consisted of pliable, tissue-engaging pads mounted on bases of more rigid plastics. The bases have been designed to be removably engaged with instrument jaws, for example by snap-action latching devices which come into locking engagement with the instrument jaws when the attachments are slid into position. It is important that the attachments be very reliable, so that they do not become detached unintentionally and fall into the patient, where their retrieval may be difficult. Designers have encountered a minimum size limit, below which the plastics bases are insufficiently strong to be reliable. Below this minimum size limit, the latch mechanisms of the plastics bases may be inadequate, or the plastics bases may break into pieces. In either case, serious untoward consequences may result.

Alternative attachment base materials, metal, for example are not entirely satisfactory for very small jaw attachments for several reasons. First, when attached to a jaw, they can be quite difficult to remove. Second, unless the metal attachment bases are made to extremely close manufacturing tolerances, they may exhibit some "play" relative to the jaws, which is undesirable, especially in laparoscopic surgery, and are subject to accidental detachment from the jaws.

This invention addresses the above-mentioned problems. Its principal object is to provide a jaw attachment which can be extremely small in size, and yet highly resistant to play, to breakage, and to inadvertent detachment from the instrument jaw on which it is mounted. Other objects of the invention include simplicity, reliability, ease of attachment and detachment, and simplicity of manufacture.

In accordance with the invention, a grasping attachment is removably mounted on at least a first jaw of an instrument having a pair of jaws capable of moving toward and away from each other. The first jaw has a surface facing toward the other jaw, a hole opening to the surface and a clip-engageable portion spaced from the hole. The grasping attachment comprises an assembly of a metal element and a plastics element, and also an elastomeric layer.

The metal element is in the form of a resilient sheet having a plate portion situated in facing relationship to the first jaw, a clip, unitary with the plate portion, and engaged with the clip-engageable portion of the first jaw, and an aperture in the plate portion. The aperture in the plate portion is aligned with the hole in the first jaw.

The plastics element comprises a substantially rigid plastics layer fixed to the plate portion of the metal element, with at least a part of the plate portion located between the plastics layer and the first jaw. The plastics element also has a projection extending from the plastics layer through the aperture in the plate portion. This projection either closely fits into the hole in the first jaw or fits into the hole with a snap fit.

The elastomeric layer is substantially less rigid than the plastics layer, and is secured to the assembly of the metal and plastics elements. At least a portion of the plastics layer is located between the elastomeric layer and the plate portion of the metal element.

The metal element lends strength and stiffness to the grasping attachment, allowing the dimensions of the attachment in the direction perpendicular to the surface of the first jaw to be minimized, and the projection of the plastics layer is sufficiently flexible to fit closely into the aperture of the first jaw without requiring excessively close manufacturing tolerances, or to fit into the aperture with a snap fit.

In a preferred version of the grasping device, the plate portion lies substantially in a plane and is elongated, having first and second ends and opposite longitudinal edges extending from the first end to the second end substantially in the direction of elongation. The clip comprises a pair of ears adjacent to the first end of the plate portion. These ears have first parts extending respectively from the opposite longitudinal edges of the plate portion, out of the plane of the plate portion. The ears also have second parts extending toward each other from the first parts. The second parts overlie the plate portion in spaced relation thereto, and the first jaw is received between the second parts and the plate portion.

The projection, which extends from the plastics layer, through the aperture in the plate portion and into the hole in the first jaw, is located closer to the second end of the plate portion than to the ears of the clip. In one embodiment, at least a portion of the projection extending beyond the plate portion has crushable ribs formed in its exterior wall. The crushable ribs are elongated in directions transverse to the plane of the plate portion, and are deformed by compression when the projection enters the hole in the jaw. The crushable ribs facilitate entry of the projection into the hole in the jaw, and establish a tight fit when the projection is situated in the hole. In another embodiment, the projection fits into the hole with a snap fit, in which case the ribs may be eliminated.

The substantially rigid plastics layer can extend laterally beyond the longitudinal edges and ends of the plate portion of the metal element. However, in a preferred embodiment, the combination of the plate portion of the metal element and the aperture therein overlies substantially the entire substantially rigid plastics layer. The longitudinal edges of the plate portion extend past the projection on opposite sides of the projection, and the plate portion is preferably shaped so that the distance between the longitudinal edges on opposite sides of the projection is greater than the distance between the longitudinal edges adjacent the location of the clip.

By virtue of the foregoing features, and especially the use of a metal element in combination with a plastics projection, the grasping attachment can be made sufficiently small to be used with jaw instruments designed to extend through cannulae having very small internal diameters, e.g. 5 mm or smaller.

Other objects, details and advantages of the invention will be apparent from the following detailed description when read in conjunction with the drawings.

DETAILED DESCRIPTION

Figure 1:
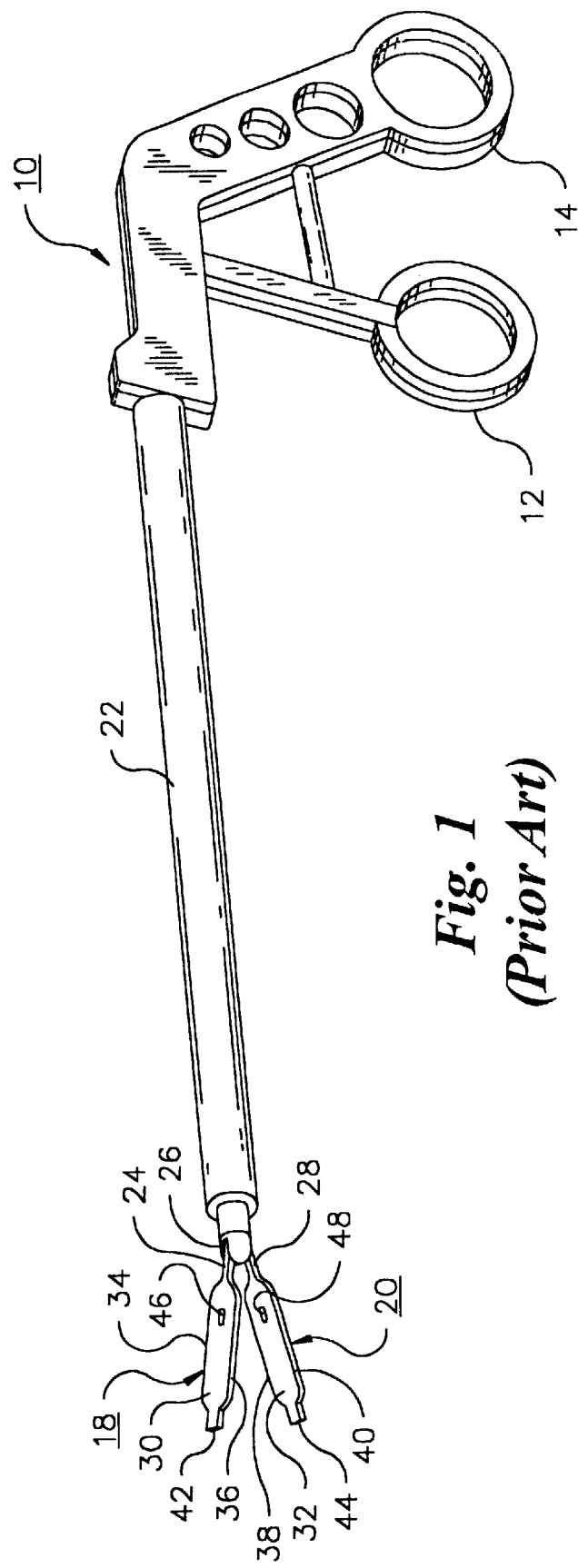
FIG. 1 is a perspective view of a typical surgical grasping device, having jaws designed for use with grasping attachments.

The instrument of FIG. 1 is a typical endoscopic forceps having a handle assembly 10 having a pair of ring handles 12 and 14, handle 12 being movable toward handle 14 to actuate the forceps jaws 18 and 20, which are situated at the opposite end of a barrel 22 from the handle. The direction from the handle assembly 10 toward the jaws will be referred to as the "distal" direction and the direction from the jaws toward the handle assembly will be referred to as the "proximal" direction.

In the preferred endoscopic forceps, a conventional linkage (not shown) located inside the handle and inside the barrel causes the jaws 18 and 20 to approach each other as the handle 12 is moved toward handle 14, and to move away from each other as the handle 12 is moved away from handle 14.

Although in most cases, both of the jaws move symmetrically relative to the barrel axis, it is possible to utilize alternative arrangements, for example, one in which only one of the jaws moves while the other remains in fixed relationship to the barrel.

As shown in FIG. 1, each of the jaws is generally in the form of an elongated metal plate extending distally from a stem. Thus, jaw 18 comprises a plate having a stem 24 extending through a slot 26 at the distal end of the barrel 22, and jaw 20 similarly comprises a plate having a stem 28 extending through slot 26. Each plate has inner and outer faces, the upper face 30 on jaw 18 being an outer face, and the upper face 32 on jaw 20 being an inner face. Each of the plates has a central portion having parallel edges, the parallel edges of the plate of jaw 18 being seen at 34 and 36, and the parallel edges of the plate of jaw 20 being seen at 38 and 40. The inner faces of the jaws are in opposed relationship to each other, and can be brought into a relationship with each other such that the inner faces are parallel to each other and spaced from each other by a distance of about 2 mm.

The plate of each jaw is tapered adjacent to its distal end and has a tip comprising parallel edges which are closer to each other than the parallel edges of the main portion of the plate. These tips are adapted to be engaged by a C-shaped clip of an attachment which will be described below. Thus jaw 18 has a tip 42, and jaw 20 has a tip 44.

The inner face of the plate of each jaw is also provided with a hole near its proximal end for receiving a projection of an attachment, as will be described. The holes are preferably, but not necessarily, through holes, hole 46 being a through hole in jaw 18 and hole 48 being a through hole in jaw 20.

The grasping attachments, which will be described with reference to FIGS. 2–5, are intended to provide a secure, but atraumatic, grip on anatomical tissue. The tissue-grasping components of the attachments are situated on the inner faces of the jaws 18 and 20. C-shaped clips, which constitute components of the attachments fit closely onto the tips 42 and 44, while projections on the attachments fit into holes 46 and 48. The attachments have resilience allowing them to be bent away from the planes of the inner faces of the jaws when the C-shaped clips are attached to the tips 42 and 44. It is this same resilience which urges the projections into the holes when the C-shaped clips are engaged with the tips, thereby securing the attachments to the jaws and preventing unintended detachment, while allowing the attachments to be removed readily by deliberate manipulation.

Figure 3:
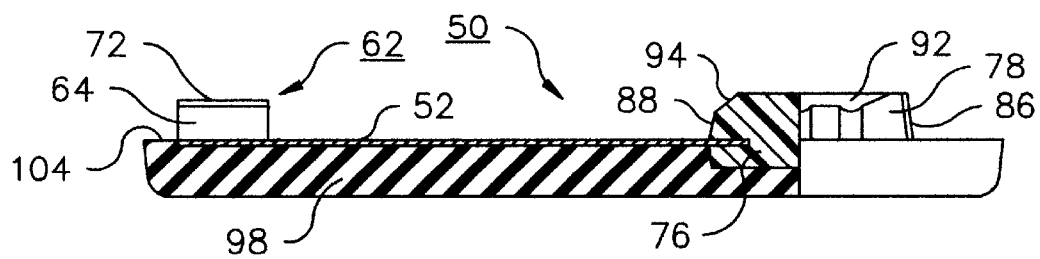
FIG. 3 is a longitudinal section of a grasping attachment taken on surface 3—3 of FIG. 2.
Figure 2:
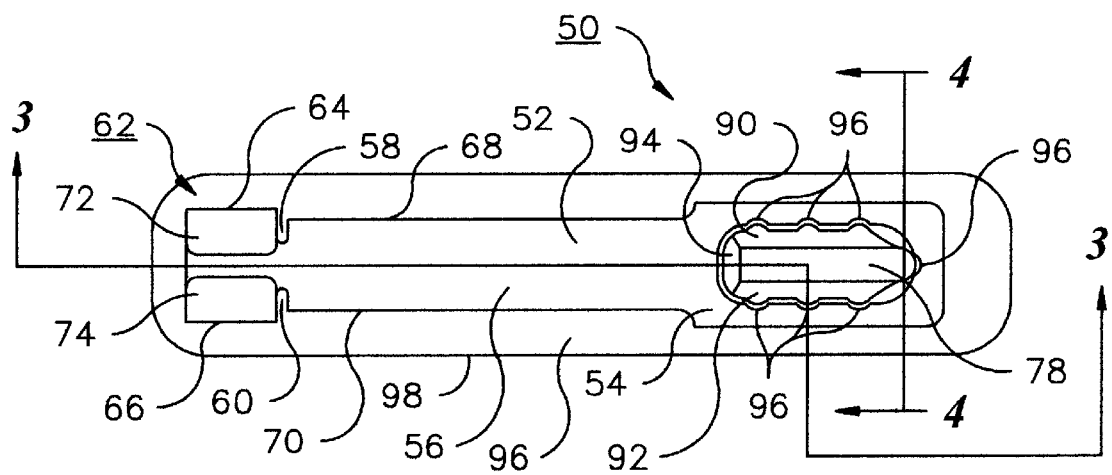
FIG. 2 is a top plan view of the grasping attachment.
Figure 4:
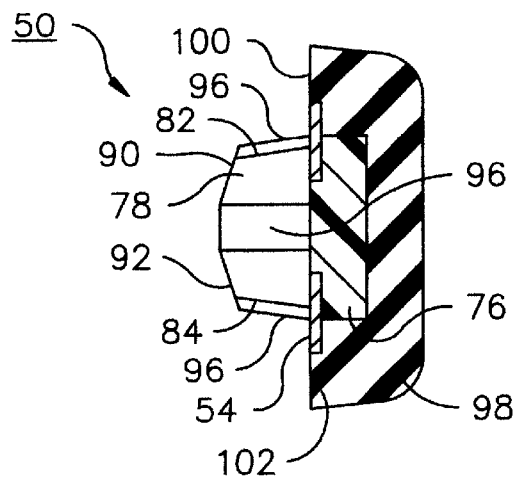
FIG. 4 is a sectional view of the grasping attachment taken on plane 4—4 in FIG. 3.

As shown in FIGS. 2, 3 and 4, the grasping attachment 50 is elongated and generally rectangular in shape. It comprises an elongated sheet metal element having a plate portion 52 with a wide part 54 adjacent to a proximal end of the attachment, a narrower part 56 extending from the wide part toward the distal end, and notches 58 and 60 spaced a short distance from the distal end. On the distal side of the notches adjacent to the distal end of the grasping attachment, the sheet metal element has ears which form a C-shaped clip 62. The ears comprise first parts 64 and 66, which extend respectively, from opposite longitudinal edges 68 and 70 of the plate, out of the plane in which plate portion 52 lies. At the upper ends of parts 64 and 66, the ears have second parts 72 and 74, which extend toward each other from the first parts and overlie the plate portion 52 in spaced relation thereto. The size of the C-shaped clip 62 is such that it can be closely fitted onto one or the other of projections 42 and 44 in FIG. 1. The notches 58 and 60 facilitate bending of the plate portion of the metal element at a location adjacent to the C-shaped clip so that the grasping element can be readily installed on, and removed from, and instrument jaw.

The sheet metal element is preferably composed of a stainless steel having enough resilience to enable the C-shaped clip to grip projection 42 or 44 tightly, and to enable the narrow part 56 of the sheet metal element to bend for connection and removal of the attachment.

A layer 76 (FIGS. 3 and 4) is situated adjacent the wide part 54 of Plate portion 52 of the sheet metal element. This layer is a substantially rigid layer, composed of a plastics material, preferably polypropylene, or another similar synthetic resin suitable for use in a surgical instrument. The layer 76 is a part of a molded element including a projection 78 which extends outwardly from the wide part 54 plate portion 52. The element is molded so that the margins of layer 76 underlie the plate portion and the projection overlies the plate portion, and consequently, the plastics element is permanently attached to the metal plate portion.

The projection is slightly tapered, having sloping sidewalls 82 and 84, as well as sloping front and rear ends 86 and 88, respectively. The top of the projection is beveled at 90, 92 and 94 to facilitate entry of the projection into hole 46 or 48, and the proximal and side walls are provided with deformable ribs 96, which, as mentioned previously, both facilitate entry of the projection into the hole in the instrument jaw and ensure a tight fit so that the grasping attachment is held firmly on the jaw.

An elastomeric pad 98, preferably made of silicone rubber, is secured to the plastics layer 76, and to the plate portion of the metal element, preferably by an adhesive (not shown). The face of the plate portion which is contacted by the pad may be etched for more effective adhesion. The pad is shaped with a rim so that it forms a recess receiving the plate portion 52. Side portions of the rim are seen in FIG. 4 at 100 and 102, and a distal portion of the rim is seen in FIG. 3 at 104.

The exposed surface of the elastomeric pad is covered by a membrane which imparts to it the ability to hold anatomical tissue effectively without causing trauma. A variety of suitable materials can be used, for example, a high-density non-woven polyethylene available under the trademark TYVEK, polymers such as polyvinyldiene fluoride (PVDF), and spunbonded materials such as a polyester membrane material, e.g. Ahlstorm's 3283 or Reemay's 2040 product. Other suitable materials are described in U.S. Pat. No. 5,728,121, the disclosure of which is incorporated by reference.

Figure 5:
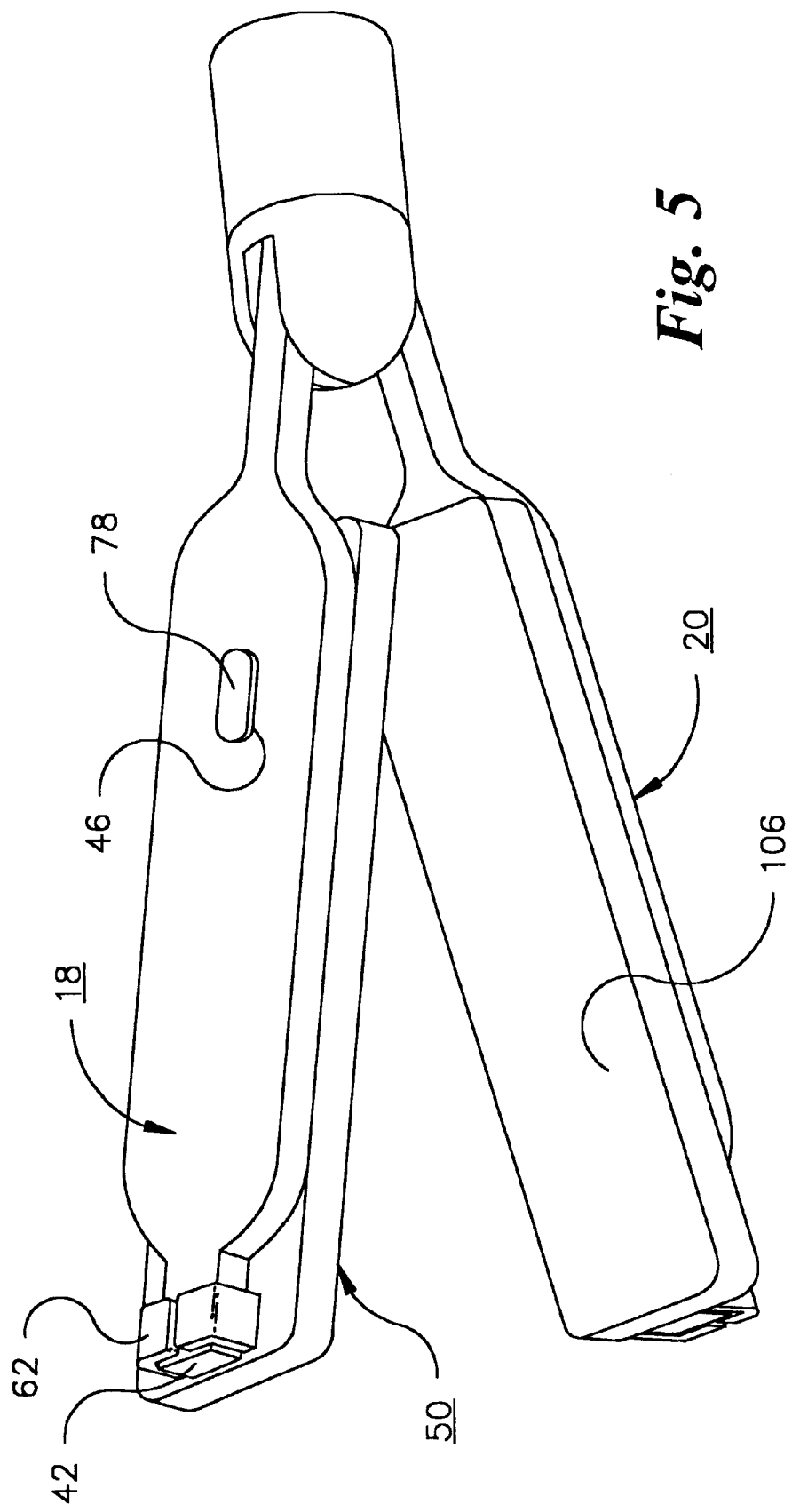
FIG. 5 is a fragmentary perspective view of the working end of a surgical grasping device of the kind shown in FIG. 1, with grasping attachments in accordance with the invention removably connected to both of its jaws.

As shown in FIG. 5, grasping attachment 50 is attached to a jaw 18 by engaging its C-shaped clip 62 with projection 42 of the jaw, and allowing projection 78 to enter hole 46 of the jaw. The spring action of the metal element holds the projection in hole 46 so that the grasping attachment is firmly secured in place on the jaw. An identical grasping attachment 106 may be secured to jaw 20 in a similar manner, so that the elastomeric pads of the two grasping attachments are in opposed relationship to each other.

The grasping attachments may be supplied pre-sterilized in sealed packages, and readily attached to the instrument of FIG. 1 prior to surgery. After use, the attachments can be removed from the jaws by bending the attachments until the projections clear the holes 46 and 48 and sliding the attachments in the distal direction until the C-shaped clips disengage the end projections 42 and 44 on the jaws. The attachments can then be discarded.

The invention makes it possible to provide extremely small, but strong and reliable grasping attachments suitable for laparoscopic surgery using cannulae having internal diameters of 5 mm or smaller.

As mentioned previously, as an alternative, the projection can be made to fit into hole 46 or 48 by a snap fit. This alternative will be described with reference to FIG. 6, in which an elastomeric pad 108, of silicone rubber or similar material, is secured to a layer 110 of a resilient plastics element 112 and also to metal plate 114. The plastics element 112 has a narrow portion 116, which extends through a hole 118 in the metal plate, and is generally similar to the structure depicted in FIGS. 3 and 4 except that the portion of the plastics element which engages the hole 46 or 48 in the instrument jaws 18 or 20 comprises two elements 120 and 122, having a gap 124 between them and outwardly projecting flanges 126 and 128, which engage the outer faces of the jaws to hold the grasping element firmly in place.

Figure 6:
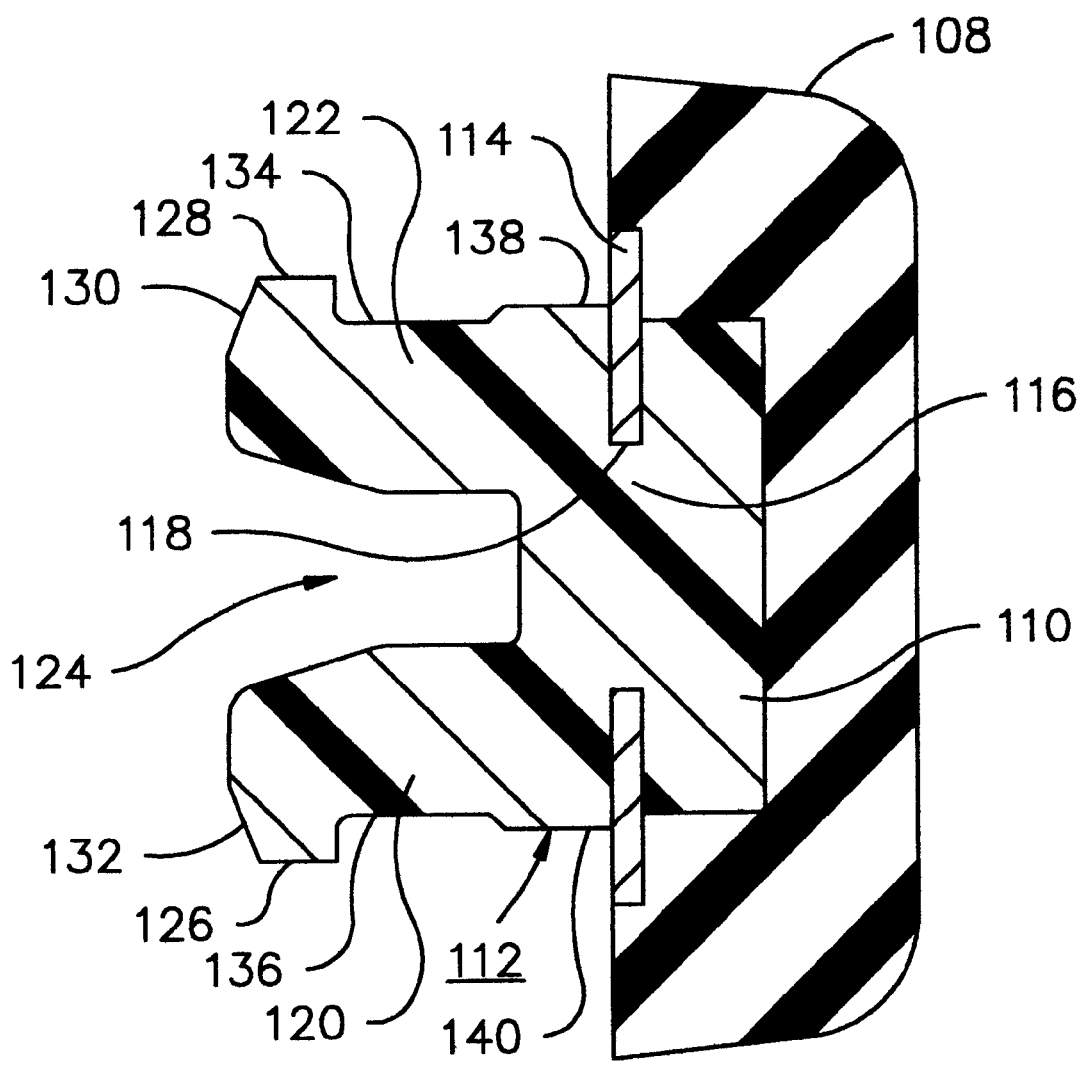
FIG. 6 is a sectional view, similar to FIG. 4, showing an alternative grasping attachment.

As seen in FIG. 6, the elements 120 and 122 are beveled at 130 and 132 so that the force exerted in pressing the plastics element 112 into a hole 46 or 48 pushes elements 120 and 122 toward each other, allowing the flanges 126 and 128 to pass through the hole. The outer faces of element 112 are configured so that the element 112 is narrower at locations 134 and 136 adjacent the flanges than at locations 138 and 140 adjacent the metal plate 114. The narrower portion of the element 112 ensure that its flanges can reliably engage the outer face of the jaw with to which it is attached with a snap fit. The wider portion at the base of element 112 fits snugly into hole 46 or 48 in the jaw to prevent movement of the grasping pad relative to the jaw. The embodiment of FIG. 6 does not rely upon resilience of the metal plate 114 for secure attachment of the grasping pad to the instrument jaws, and is a preferred embodiment for most applications.

Various other modifications can be made to the grasping attachment described. For example, the plastics layer can be made larger, and can even be made coextensive with the elastomeric layer, in which case the elastomeric layer is attached primarily to the plastics layer. Additional molded projections, which fit into holes in the metal layer but do not extend beyond the metal layer, can be used to supplement a projection corresponding to projection 78 in securing the plastics layer to the metal layer.

Still other modifications may be made to the apparatus and method described above without departing from the scope of the invention as defined in the following claims.

What is claimed is:

1. A surgical grasping device comprising:
   a grasping attachment removably mountable on the jaw of a surgical instrument, the grasping attachment comprising an assembly of a metal element and a plastics element;
   the metal element being in the form of a resilient sheet having a plate portion, a clip, unitary with the plate portion, and engageable with a clip-engageable portion of an instrument jaw, and an aperture, in the plate portion, and alignable with a hole in an instrument jaw; and
   the plastics element comprising a substantially rigid plastics layer fixed to the plate portion of the metal element, with at least a part of the plate portion being locatable between the plastics layer and an instrument jaw, the plastics element having a projection extending from said plastics layer through the aperture in the plate portion, and beyond the plate portion, for entry into a hole in the instrument jaw; and
   an elastomeric layer, substantially less rigid than said plastics layer, secured to said assembly of a metal element and a plastics element, at least a portion of the plastics layer being located between the elastomeric layer and the plate portion of the metal element;
   whereby the metal element lends strength and stiffness to the grasping attachment, allowing the dimensions of the attachment in directions perpendicular to said sheet portion to be minimized; and the projection of the plastics layer is sufficiently flexible to fit closely into an aperture of a jaw without requiring excessively close manufacturing tolerances.

2. A surgical grasping device according to claim 1, in which the plate portion lies substantially in a plane and is elongated, having first and second ends and opposite longitudinal edges extending from the first end to the second end substantially in the direction of elongation, and in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto.

3. A surgical grasping device according to claim 1, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto, and in which the projection is located closer to said second end of the plate portion than to said ears.

4. A surgical grasping device according to claim 1, in which the plate portion lies substantially in a plane, in which at least a portion of the projection of the plastics element extending beyond the plate portion has an exterior wall with crushable ribs formed therein, the crushable ribs being elongated in directions transverse to the plane of said plate portion.

5. A surgical grasping device according to claim 1, in which the plate portion lies substantially in a plane, in which at least a portion of the projection of the plastics element extending beyond the plate portion has an exterior wall with laterally projecting flanges, spaced from said plate portion, for securing the grasping attachment to a jaw with a snap fit.

6. A surgical grasping device according to claim 1, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto, and in which at least a portion of the projection of the plastics element extending beyond the plate portion has an exterior wall with crushable ribs formed therein, the crushable ribs being elongated in directions transverse to the plane of said plate portion.

7. A surgical grasping device according to claim 1, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto, and in which at least a portion of the projection of the plastics element extending beyond the plate portion has an exterior wall with laterally projecting flanges, spaced from said plate portion, for securing the grasping attachment to a jaw with a snap fit.

8. A surgical grasping device according to claim 1, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto, in which at least a portion of the projection of the plastics element extending beyond the plate portion has an exterior wall with crushable ribs formed therein, the crushable ribs being elongated in directions transverse to the plane of said plate portion, and in which the projection is located closer to said second end of the plate portion than to said ears.

9. A surgical grasping device according to claim 1, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto, in which at least a portion of the projection of the plastics element extending beyond the plate portion has an exterior wall with laterally projecting flanges, spaced from said plate portion, for securing the grasping attachment to a jaw with a snap fit, and in which the projection is located closer to said second end of the plate portion than to said ears.

10. A surgical grasping device comprising:

first and second jaws mounted for movement toward and away from each other, the first jaw being a rigid jaw having a surface facing toward the second jaw, a hole opening to said surface and a clip-engageable portion spaced from said hole;

a grasping attachment removably mounted on said first jaw, the grasping attachment comprising an assembly of a metal element and a plastics element;

the metal element being in the form of a resilient sheet having a plate portion situated in facing relationship to the first jaw, a clip, unitary with the plate portion, and engaged with the clip-engageable portion of the first jaw, and an aperture, in the plate portion, and aligned with said hole in the first jaw; and the plastics element comprising a substantially rigid plastics layer fixed to the plate portion of the metal element, with at least a part of the plate portion being located between the plastics layer and the first jaw, the plastics element having a projection extending from said plastics layer through the aperture in the plate portion and closely fitting into said hole in the first jaw; and an elastomeric layer, substantially less rigid than said plastics layer, secured to said assembly of a metal element and a plastics element, at least a portion of the plastics layer being located between the elastomeric layer and the plate portion of the metal element;

whereby the metal element lends strength and stiffness to the grasping attachment, allowing the dimensions of the attachment in the direction perpendicular to said surface of the first jaw to be minimized; and the projection of the plastics layer is sufficiently flexible to fit closely into the aperture of the first jaw without requiring excessively close manufacturing tolerances.

11. A surgical grasping device according to claim 10, in which the plate portion lies substantially in a plane and is elongated, having first and second ends and opposite longitudinal edges extending from the first end to the second end substantially in the direction of elongation, and in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto, and the first jaw being received between said second parts and said plate portion.

12. A surgical grasping device according to claim 10, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto and the jaw being received between said second parts and said plate portion, and in which the projection is located closer to said second end of the plate portion than to said ears.

13. A surgical grasping device according to claim 10, in which the plate portion lies substantially in a plane, in which at least a portion of the projection of the plastics element extending beyond the plate portion has an exterior wall with crushable ribs formed therein, the crushable ribs being elongated in directions transverse to the plane of said plate portion.

14. A surgical grasping device according to claim 10, in which the plate portion lies substantially in a plane, in which at least a portion of the projection of the plastics element extending beyond the plate portion has an exterior wall with laterally projecting flanges, spaced from said plate portion, for securing the grasping attachment to a jaw with a snap fit.

15. A surgical grasping device according to claim 10, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto, and in which at least a portion of the projection of the plastics element extending beyond the plate portion has an exterior wall with crushable ribs formed therein, the crushable ribs being elongated in directions transverse to the plane of said plate portion.

16. A surgical grasping device according to claim 10, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto, and in which at least a portion of the projection of the plastics element extending beyond the plate portion has an exterior wall with laterally projecting flanges, spaced from said plate portion, for securing the grasping attachment to a jaw with a snap fit.

17. A surgical grasping device according to claim 10, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto and the first jaw being received between said second parts and said plate portion, in which at least a portion of the projection of the plastics element extending beyond the plate portion has an exterior wall with crushable ribs formed therein, the crushable ribs being elongated in directions transverse to the plane of said plate portion, and in which the projection is located closer to said second end of the plate portion than to said ears.

18. A surgical grasping device according to claim 10, in which the plate portion lies substantially in a plane and is elongated, having first and second ends and opposite longitudinal edges extending from the first end to the second end substantially in the direction of elongation, in which the clip comprises a pair of ears adjacent to said first end, the ears having first parts extending respectively from the opposite longitudinal edges out of the plane of the plate portion, and second parts extending toward each other from the first parts, the second parts overlying the plate portion in spaced relation thereto and the first jaw being received between said second parts and said plate portion, in which at least a portion of the projection of the plastics element extending beyond the plate portion has an exterior wall with laterally projecting flanges, spaced from said plate portion, for securing the grasping attachment to a jaw with a snap fit, and in which the projection is located closer to said second end of the plate portion than to said ears.

\* \* \* \* \*